United States Patent [19]
Drent et al.

[11] Patent Number: 6,080,898
[45] Date of Patent: Jun. 27, 2000

[54] HYDROGENOLYSIS OF GLYCEROL

[75] Inventors: Eit Drent; Willem Wabe Jager, both of Amsterdam, Netherlands

[73] Assignee: Shell Oil Company, Houston, Tex.

[21] Appl. No.: 09/121,465

[22] Filed: Jul. 23, 1998

[30] Foreign Application Priority Data

Jul. 23, 1997 [EP] European Pat. Off. .............. 97305508

[51] Int. Cl.[7] ............................. C07C 31/18; C07C 47/22
[52] U.S. Cl. ............................ 568/861; 568/449; 568/486
[58] Field of Search ..................................... 568/449, 486, 568/492, 861, 862, 863

[56] References Cited

U.S. PATENT DOCUMENTS 4,642,394  2/1987  Che ........................................ 568/861

FOREIGN PATENT DOCUMENTS 9505354  2/1995  WIPO .

*Primary Examiner*—Sreeni Padmanabhan

[57] ABSTRACT

A process for the catalytic hydrogenolysis of glycerol in the presence of a homogeneous catalyst that is based on a platinum group metal or a compound of a platinum group metal, an anion source, and a metal-complexing compound of the formula $Q^1Q^2MQ^3$ (I) or $Q^1Q^2MQMQ^3Q^4$ (II) wherein M represents phosphorus, arsenic or antimony, Q represents a group that is covalently bonded to both M's and having at least two carbon atoms in the bridge and $Q^1$ to $Q^4$ are independently similar or dissimilar optionally substituted hydrocarbyl groups or $Q^1$ and $Q^2$ and/or $Q^3$ and $Q^4$ represent similar or dissimilar optionally substituted hydrocarbylene groups.

8 Claims, No Drawings

HYDROGENOLYSIS OF GLYCEROL

BACKGROUND OF THE INVENTION

The invention relates to a process for the catalytic hydrogenolysis of glycerol. In particular, the invention relates to the preparation of propylene glycols (1,2- and 1,3-propanediols) and/or acrolein by the hydrogenolysis of glycerol.

Propylene glycols and acrolein are valuable chemicals. For instance, 1,3-propanediol (PDO) is an attractive monomer in the preparation of polyesters and polyurethanes. It may also be used to prepare cyclic ethers that find use as solvent. Likewise, acrolein and its dimer provide a valuable starting point for the synthesis of chemicals used in textile finishing, paper treating, and the manufacture of rubber chemicals, pharmaceuticals, plasticizers and synthetic resins. Propylene glycols and acrolein may be prepared by a variety of processes. For example, PDO may be prepared by the hydroformylation of ethylene oxide, or by the hydrogenation of 3-hydroxypropionaldehyde. However, each of these processes requires chemicals as starting point that have to be prepared separately, often at considerable costs. Besides, the starting chemicals may find other higher-value uses.

The chemicals industries have realised that our petrochemical resources are not unlimited. Therefore, they focused and still focus on natural resources as starting point for their processes. For instance, U.S. Pat. No. 4,642,394 describes the process for the conversion of glycerol to lower oxygenated hydrocarbons, such as 1,2- and 1,3-propanediol, by reacting glycerol with carbon monoxide and hydrogen (in a "hydrogenolysis" reaction) in the presence of a homogeneous catalyst containing tungsten and Group VIII metal components. The examples of this patent document, however, reveal the need for elevated temperatures and pressure conditions (200 centigrade, 4600 psig). The process is therefore not quite as attractive as it could be.

The art also includes examples of hydrogenolysis processes using heterogeneous catalysts. For instance, DE-A-4,302,464 describes the conversion of glycerol into 1,2-propanediol and other products (but not 1,3-propanediol) using copper chrome tablets at various elevated temperatures and pressures. U.S. Pat. No. 5,326,912 employs a catalyst containing ruthenium, palladium and copper. However, glycerol is produced rather than converted.

It is therefore an object of the invention to provide a process for the conversion of glycerol to lower oxygenated hydrocarbons which avoids the need for these elevated temperature and pressure conditions.

BRIEF SUMMARY OF THE INVENTION

According to the invention, a process is provided for the catalytic hydrogenolysis of glycerol in the presence of a homogeneous catalyst that is based on a platinum group metal or a compound of a platinum group metal, an anion, and a metal-complexing compound of the formula $Q^1Q^2MQ^3$ (I) or $Q^1Q^2MQMQ^3Q^4$ (II) wherein M represents phosphorus, arsenic or antimony, Q represents a group that is covalently bonded to both M's and having at least two atoms in the bridge and $Q^1$ to $Q^4$ are independently similar or dissimilar optionally substituted hydrocarbyl groups or $Q^1$ and $Q^2$ and/or $Q^3$ and $Q^4$ represent similar or dissimilar optionally subsituted hydrocarbylene groups.

Note that the standard textbook "Advanced Organic Chemistry", by Jerry March (3rd ed., pages 392–393) in respect of hydrogenolysis of alcohols mentions that "the hydroxyl groups of most alcohols can seldom be cleaved". Examples that do undergo the reaction readily are benzyl-type alcohols. In addition, 1,3-glycols are mentioned as being especially susceptible to hydrogenolysis, whereas tertiary alcohols can be reduced by catalytic hydrogenolysis when the catalyst is platinum bis(triphenylphosphine) dichloride. It is therefore surprising that glycerol, which is not a benzyl-type alcohol, may be converted into propylene glycols and/or acrolein. Moreover, it is surprising that the conversion of glycerol may be controlled to stop at the stage where the propylene glycols and/or the acrolein are produced.

DETAILED DESCRIPTION OF THE INVENTION

In the present specification the metals of the platinum group are defined as the metals with the atomic numbers 28, 46 and 78, i.e. nickel, palladium and platinum. Of these, palladium and platinum are preferred.

Examples of suitable metal sources are metal nitrates, suphates, sulphonates, metal salts carboxylic acids with up to 12 carbon atoms, or inorganic metal complexes, e.g. with carbon monoxide or acetylacetonate. Palladium(II) acetate and platinum(II) acetylacetonate are examples of preferred metal sources.

The anion on which the catalyst is based may be obtained from sources such as acids and salts. The anion may also stem from platinum group metal salts, in which case both catalyst components are provided by the same source.

Preferred anion sources in the catalyst systems of the present invention are strong acids, i.e., acids having a pKa value of less than 3, preferably less than 2, measured in aqueous solution at 18° C. The anions derived from these acids are non-coordinating or weakly coordinating with the metals of the platinum group.

Typical examples of suitable anions are anions of phosphoric acid, sulphuric acid, hydrogen halides, sulphonic acids and halogenated carboxylic acids such as trifluoroacetic acid. Sulphonic acids are in particular preferred, for example methanesulphonic acid, trifluoromethanesulphonic acid, tert-butanesulphonic acid, p-toluenesulphonic acid and 2,4,6-trimethylbenzenesulphonic acid. Halide anions have been found particularly useful (in combination with other anions) when water is applied as reaction solvent.

Also, complex anions are suitable, such as the anions generated by a combination of a Lewis acid such as $BF_3$, $AlCl_3$, $SnF_2$, $Sn(CF_3SO_3)_2$, $SnCl_2$ or $GeCl_2$, with a protic acid, such as a sulphonic acid, e.g. $CF_3SO_3H$ or $CH_3SO_3H$ or a hydrogen halide such as HF of HCl, or a combination of a Lewis acid with an alcohol. Examples of such complex anions are $BF_4^-$, $SnCl_3^-$, $[SnCl_2.CF_3SO_3]^-$ and $PF_6^-$.

Finally, also mixtures of anions may be used; in particular the mixture of halide anions in combination with another anion source mentioned above.

In the metal-complexing compounds of formula (I) or (II), (each) M is a phosphorus atom, in which case the compounds are monophosphines or bisphosphines.

Preferably, a metal-complexing compound of the general formula (II) is used. The bridging group in such a compound, represented by Q, typically is composed of carbon atoms. Preferably the bridging group contains two or three carbon atoms in the bridge.

The hydrocarbyl groups $Q^1$ to $Q^4$ may independently represent various non-cyclic or cyclic groups of up to 20 carbon atoms, preferably up to 15 carbon atoms, more preferably up to 10 carbon atoms, optionally substituted with substituents such as alkoxy groups with 1 to 4 carbon atoms, halogen atoms or ($C_1$ to $C_4$ alkyl)amino groups. Examples are alkyl groups such as ethyl, isopropyl, sec-butyl and tert-butyl groups, cycloalkyl groups such as cyclopentyl and cyclohexyl groups, and aryl groups such as phenyl, tolyl and naphthyl groups.

In view of the higher activity of the resulting catalyst system, $Q^1$ together with $Q^2$, and in case of a compound of general formula (II) $Q^3$ together with $Q^4$, preferably represent an optionally substituted hydrocarbylene group. The hydrocarbylene group in general comprises at least 5 ring atoms and preferably contains from 6 to 9 ring atoms. More preferably the cyclic group contains 8 ring atoms. Substituents, if any, are alkyl groups having from 1 to 4 carbon atoms. As a rule, all ring atoms are carbon atoms, but bivalent cyclic groups containing one or two heteroatoms in the ring, such as oxygen- or nitrogen atoms, are not precluded. Examples of suitable bivalent cyclic groups are 1,4-cyclohexylene, 1,4-cycloheptylene, 1,3-cycloheptylene, 1,2-cyclooctylene, 1,3-cyclooctylene, 1,4-cyclooctylene, 1,5-cyclooctylene, 2-methyl-1,5-cyclooctylene, 2,6-dimethyl-1,4-cyclooctylene and 2,6-dimethyl-1,5-cyclooctylene groups.

The preferred metal-complexing compounds of formula (II) are 1,2-bis(1,4-cyclooctylenephosphino)-ethane, 1,2-bis (1,5-cyclooctylenephosphino)ethane and mixtures thereof. For the preparation of these compounds, reference is made to known techniques, for example the method disclosed in GB-A-1,127,965.

The quantity in which the catalyst system is used, is not critical and may vary within wide limits. Usual amounts range from $10^{-8}$ to $10^{-1}$, preferably from $10^{-7}$ to $10^{-2}$ mole atom of platinum group metal per mole of ethylenically unsaturated compound. The amounts of the participants in the catalyst system are conveniently selected such that per mole atom of platinum group metal from 0.5 to 10, preferably from 1 to 6 moles of metal-complexing compound ligand are used, and from 0.5 to 15, preferably from 1 to 8 moles of anion source or a complex anion source are used.

Typically, the hydrogenolysis process is carried out under an atmosphere that comprises or is composed of hydrogen gas. For instance, an atmosphere of carbon monoxide and hydrogen is quite suitable. These gases may be present in equimolar or non-equimolar ratios, e.g. in a ratio within the range of 5:1 to 1:5.

The hydrogenolysis can be carried out at moderate reaction conditions. Hence temperatures in the range of 50 to 250° C. are recommended, preferred temperatures being in the range of 70 to 200° C. Reaction pressures in the range of 5 to 100 bar are preferred. Lower or higher pressures may be selected, but are not considered particularly advantageous. Moreover, higher pressures require special equipment provisions.

In the process of the invention, the starting material and the formed product may act as reaction diluent. Hence, the use of a separate solvent is not necessary. However, the hydrogenolysis reaction is conveniently carried out in the additional presence of a solvent. As such, saturated hydrocarbons, e.g. paraffins and isoalkanes are recommended and furthermore alcohols, preferably having from 3 to 10 carbon atoms per molecule, such as propanol, butanol, ethylhexanol-1, nonanol-1, or in general terms the alcohols formed as hydrogenolysis product; ethers such as 2,5,8-trioxanonane (diglyme), diethylether and anisole, and ketones, such as methylbutylketone. A particularly suitable solvent or cosolvent is water. Solvents comprising or substantially consisting of sulphones are also quite suitable. Particular preferred sulphones are, for example, dialkylsulphones such as dimethylsulphone and diethylsulphone and cyclic sulphones, such as sulfolane (tetrahydrothiophene-2, 2-dioxide), sulfolene, 2-methylsulfolane and 2-methyl-4-ethylsulfolane. Mixtures of solvents may also be used, for example a mixture of a sulphone with a protic solvent, such as an alcohol or water.

The amount of solvent to be used in the process of the invention may vary considerably. The experimental results provided hereinafter are indicative for the amount of solvent preferably to be used.

The invention will be illustrated by the non-limiting examples, as described hereinafter. The abbreviations, used in the Tables have the following meanings:

BCPE=1,2-bis(1,5-cyclooctylenephosphino)ethane
BBPE=1,2-bis(sec-butylphosphino)ethane
MSA=methanesulphonic acid
TFSA=trifluoromethanesulphonic acid

EXAMPLES 1 TO 5

The experiments were carried out in a 250 ml magnetically stirred autoclave. The autoclave was charged with 30 ml glycerol, sulfolane and water in the amounts disclosed in the Table, 0.25 mmol of palladium(II) acetate, 0.6 mmol of complexing compound and anions again in the amount disclosed in the table. After being flushed, the autoclave was pressurized. Subsequently, the reactor was sealed and the contents were heated to the pre-set temperature and maintained at that temperature for 10 hours. After cooling, a sample was taken from the contents of the reactor and analysed by Gas Liquid Chromatography. Further details and the results of the analysis can be found in the Table.

The calculated conversion rate is expressed as moles of product per mole atom of platinum group metal and per hour, (mol/mol.h).

COMPARATIVE EXAMPLE 1

The experiment was performed substantially according to the procedure as described above, however using 1.0 g of a heterogeneous Pd on carbon catalyst (10% Pd on C, ex. Janssen Chimica), 40 ml of glycerol and an atmosphere of pure hydrogen gas (which should afford a better yield). The results are also set out in the Table.

COMPARATIVE EXAMPLE 2

The experiment was performed substantially according to the procedure as described above, however using 1.0 g of a heterogeneous Ru on carbon catalyst (5% Ru on C, ex. Janssen Chimica), 40 ml of glycerol and an atmosphere of pure hydrogen gas. The results are also set out in the Table.

COMPARATIVE EXAMPLE 3 AND 4

The experiment was performed substantially according to the procedure as described in example 1 of U.S. Pat. No. 4,642,394 at the conditions mentioned above.

The autoclave was charged with 50 ml 1-methyl-2-pyrrolidinone, 20 ml glycerol, 0.58 mmol $Rh(CO)_2$ acetylacetonate, and 4 mmol $H_2WO_4$. The reactor is heated to about 150° C. and maintained at 60 bar of 1:2 ($CO:H_2$) synthesis gas. After 15 hours only traces of acrolein could be detected.

When the Group 10 metal was replaced by $Pd(CO)_2$ acetylacetonate, no products could be detected at all.

CONCLUSIONS

Although not optimised, the examples according to the invention outperform the comparative examples. Other remarks than can be made concern the metal-complexing compound. Thus, the preferred BCPE affords a catalyst system with a higher rate than the one based on BBPE. The acidity to the anion source affects the rate and selectivity to acrolein. The rate is also improved by the presence of halide anions. Whereas the amount of water allows some control in respect of selectivity.

TABLE I

| Example. No | Ligand | Anion source (mmol) | Solvent (ml) | Temp. (° C.) | CO/H2 (bar) | Rate (mol/mol.h) | Selectivity (%) A/B/C/D |
|---|---|---|---|---|---|---|---|
| 1 | BCPE | MSA (5) | sulpholane (10) + water (10) | 140 | 20/40 | 12.8 | —/47.4/21.8/30.8 |
| 2 | BCPE | MSA (2) + HCl (0.2) | sulpholane (10) + water (5) | 170 | 30/30 | 31.2 | 1.6/61.6/15.8/21.0 |
| 3 | BCPE | MSA (2) + HI (0.2) | sulpholane (10) + water (5) | 170 | 20/40 | 23.5 | 4.2/88.8/3.5/3.5 |
| 4 | BCPE | TFSA (2) + HCl (0.2) | sulpholane (10) + water (5) | 175 | 20/40 | 82.5 | 79.3/15.9/0.8/4.0 |
| 5 | BBPE | MSA (2) | water (10) | 170 | 20/40 | 19.4 | 0.8/56.8/21.2/21.2 |
| C1 | — | TFSA (2) | water (5) | 150 | —/50 | <5 | traces A & B |
| C2 | — | MSA (5) | water (50) | 170 | —/50 | <5 | traces B |

A = acrolein; B = 1-propanol; C = 1,2-propanediol; D = 1,3-propanediol

What is claimed is:

1. In a process for the catalytic hydrogenolysis of glycerol in the presence of a homogeneous catalyst, the improvement wherein the homogeneous catalyst is based on a platinum group metal or a compound of a platinum group metal, an anion source, and a metal-complexing compound of the formula $Q^1Q^2MQ^3$ (I) or $Q^1Q^2MQMQ^3Q^4$ (II) wherein M represents phosphorus, arsenic or antimony, Q represents a group that is covalently bonded to both M's and has at least two carbon atoms in the bridge, and $Q^1$ to $Q^4$ are independently similar or dissimilar optionally substituted hydrocarbyl groups or $Q^1$ and $Q^2$ and/or $Q^3$ and $Q^4$ together represent similar or dissimilar optionally substituted hydrocarbylene groups; wherein the process is carried out at a temperature in the range of 50 to 250° C. and at a pressure in the range of 5 to 100 bar.

2. The process of claim 1 wherein the platinum group metal is platinum or palladium.

3. The process of claim 1 wherein an acid having a pKa value of less than 3, measured in aqueous solution at 18° C., is the anion source.

4. The process of claim 1 that is carried out in the presence of a catalyst system comprising a halide anion as the anion source.

5. The process of claim 1 wherein each M in the metal-complexing compound is phosphorus.

6. The process of claim 1 wherein a metal-complexing compound of formula (II) is used.

7. The process of claim 1 wherein $Q^1$ together with $Q^2$, and in case of a compound of general formula (II) $Q^3$ together with $Q^4$, represent an optionally substituted hydrocarbylene group.

8. The process of claim 1 that is carried out in the presence of sulpholane, water or a mixture thereof.

* * * * *